United States Patent [19]

Rosenblum

[11] 4,176,031
[45] Nov. 27, 1979

[54] DIGITAL HYPOCHLOROUS ACID ANALYZER

[75] Inventor: Richard Rosenblum, Doylestown, Pa.

[73] Assignee: Fischer & Porter Co., Warminster, Pa.

[21] Appl. No.: 887,482

[22] Filed: Mar. 17, 1978

[51] Int. Cl.$^2$ .............................................. G01N 27/46
[52] U.S. Cl. ........................ 204/195 R; 204/195 G; 204/1 T
[58] Field of Search .......... 204/1 B, 1 T, 1 H, 195 R, 204/195 G

[56] References Cited

U.S. PATENT DOCUMENTS

| | | | |
|---|---|---|---|
| 3,413,199 | 11/1968 | Morrow | 204/195 R |
| 3,556,950 | 1/1971 | Dahms | 204/195 R |
| 3,723,712 | 3/1973 | Komline et al. | 204/195 R |
| 3,902,982 | 9/1975 | Nakagawa | 204/195 R |
| 3,956,094 | 5/1976 | Capuano | 204/195 R |
| 3,959,087 | 5/1976 | Morrow | 204/1 B |
| 3,966,413 | 6/1976 | Marinenko | 204/195 R |
| 3,969,209 | 7/1976 | Mueller | 204/195 R |
| 3,979,665 | 9/1976 | Ebling et al. | 204/195 R |

Primary Examiner—T. Tung

[57] ABSTRACT

An analyzer for continuously and accurately measuring the hypochlorous acid content of chlorinated water containing free available chlorine having a hypochlorous acid component (HOCl) which is a highly reactive disinfectant and a less reactive hypochlorite ion component (OCl$^-$). To make this determination, a sample of the chlorinated water is sensed by three probes—one yielding an analog signal representing the free available chlorine content (FAC) of the sample; the second, an analog signal representing the pH of the sample; the third, an analog signal representing the sample temperature (T). These signals are digitized and applied as input data to a digital computer wherein the percentage of HOCl in the sample at a reference temperature is established on the basis of the pH data by consulting a memory storing the relationship between the percentages of HOCl and OCl$^-$ in a range of pH values. The percentage of HOCl so established is then corrected on the basis of the T data by consulting a memory storing the relationship between temperature and the equilibrium constant of HOCl. Finally, the temperature-corrected percentage of HOCl is multiplied by the FAC data to determine the HOCl content of the sample.

9 Claims, 4 Drawing Figures

DIGITAL HYPOCHLOROUS ACID ANALYZER

BACKGROUND OF INVENTION

This invention relates generally to the measurement of hypochlorous acid, and more particularly to an in-line analyzer for continuously and accurately determining the hypochlorous acid content of chlorinated water.

Disinfection of water in drinking water supplies, swimming pools, industrial process and cooling waters and waste-waters is essential to health and safety, for disinfection serves to destroy pathogens and other organisms present therein. The most widely used method of disinfection is chlorination. This involves continuously feeding either chlorine gas, calcium hypochlorite or sodium hypochlorite into the water at a controlled and regulated rate in a sufficient quantity to impart and to maintain a chlorine residual of specified type and quantity.

The quantity of any selected chlorination agent that must be applied is referred to as the "dosage." This dosage quantity, in turn, includes not only the quantity of the chlorination agent required to impart to the water the specified chlorine residual but also includes the quantity of chlorination agent required to satisfy the chlorine demand of the water. By convention, all three of these distinct quantities—the demand quantity, the residual quantity, and the dosage quantity—are expressed in parts per million (ppm); i.e., parts or chlorine per million parts of water.

The chlorine demand is the ppm chlorine that is required to destroy all harmful bacteria and to react with any oxidizable organic or inorganic chemical substances present in the water. The chlorine demand value is also related to the pH of the water, the temperature of the water, and the particular type of chlorine residual desired.

Chlorine residual is the ppm chlorine present in the water in a form which is either immediately available or potentially available to react with pollutants introduced into the water. Chlorine residual is of two types: free available chlorine residual, the form immediately available for reaction; and combined available chlorine residual, the form potentially available for reaction.

Free available chlorine is created when chlorine gas dissolves in water. In this form, chlorine is extremely reactive and is highly effective as a disinfectant. Combined available chlorine is chlorine which is present in the form of one of the chloramine compounds. This series of compounds results from the reaction of chlorine and ammonia or some nitrogeneous organic compound. In the chloramine form, the reactivity of the chloramine is reduced considerably.

Since free available chlorine is a far more powerful disinfectant than combined available chlorine, it has heretofore been the practice to continuously monitor the free chlorine residual in the water to be sure that adequate disinfection is maintained. Commonly used for this purpose is an in-line analyzer of the type described in the Morrow U.S. Pat. No. 3,959,087, wherein a sample stream of water to be tested is conducted through an amperometric cell having spaced measuring and counter-electrodes. By impressing a voltage across the electrodes causing this cell to operate in a saturation zone, the current flow through the cell becomes a function of the free available chlorine content of the stream being tested and is independent of the combined available chlorine content.

A commercially-available instrument that is capable of discriminating between free available chlorine and combined available chlorine residual to provide a continuous reading of the free chlorine content of chlorinated water is the "Anachlor" Residual Chlorine Analyzer-Transmitter manufactured by Fischer & Porter of Warminster, Pa. This instrument is described in the Fischer & Porter Instruction Bulletin 17B4200, Revision B, published in 1975.

An Anachlor instrument is not, however, capable of discriminating between the hypochlorous acid (HOCl) component of free available chlorine and the other fraction which is hypochlorite ions (OCl$^-$). The HOCl species is more active as an oxidizing and disinfecting agent than OCl$^-$, and it therefore becomes desirable to monitor the HOCl component so that by specifically sensing this process variable, one can regulate the dosage so as to maintain optimum disinfection conditions.

To this end, one must be able to select the HOCl component from the free available chlorine residual. One commercially-available instrument which is designed to carry out in situ measurements of HOCl in wter is the "Delta Chlorine Analyzer" manufactured by Delta Scientific Company of Lindenhurst, N.Y. The crucial element in this analyzer is a polarographic membrane electrode that renders the instrument selectively responsive to the chlorine species whereby its primary response is due to HOCl and its smaller secondary responses are to relatively weak chlorine disinfectants such as OCl$^-$ and chloramines.

One of the problems encountered with an instrument of the Delta type is the tendency of the membrane to absorb water by osmosis. This produces osmotic swelling of the HOCl permeable member and results in failure of the sensor when the membrane ruptures. Moreover, since the Delta instrument does not take into account the effect of variations in temperature and pH factor in HOCl, the instrument is unreliable and inaccurate in operation.

SUMMARY OF INVENTION

In view of the foregoing, the main object of this invention is to provide a digital analyzer adapted to continuously measure the hypochlorous acid content of chlorinated water, the instrument taking into account all factors which come into play in determining the HOCl content and therefore yielding an accurate and reliable reading.

A significant advantage of an analyzer in accordance with the invention is that the variables are sensed by standard probes, the analyzer being usable not only for measuring the HOCl content in a given process, but also for transmitting data for effecting automatic control of this variable, thereby making possible complete control of the disinfection process. The analyzer is not only capable of operating as a self-contained unit, but also may be tied in with a host computer.

Yet another object of this invention is to provide a highly compact and efficient analyzer of the above type whose sensing probes cooperate with a microprocessor and other integrated circuit components of a digital computer that function to carry out logical and arithmetic operations on the data yielded by the probes whereby the instrument may be manufactured at relatively low cost, using commercially-available, mass-produced micro-computer components.

Briefly stated, these objects are accomplished in an analyzer for measuring the HOCl content of chlorinated water, which analyzer effects this determination by means of three sensor probes, one yielding an analog signal representing the free available chlorine content (FAC) of the water sample being tested, the second yielding an analog signal representing the pH of the sample, and the third the temperature (T) of the sample.

These signals are digitized and applied as input data into the microprocessor of a micro-computer which includes a first read-only memory that stores the relationship existing at a reference temperature between the percentages of HOCl and OCl$^-$ in a range of pH values, and a second read-only memory that stores the relationship existing between temperature and the equilibrium constant K of HOCl. The computer is programmed to consult the first memory to establish, on the basis of the input pH data, the percentage of HOCl in the sample, and to consult the second memory on the basis of the input data to modify the established percentage to provide a corrected-percentage value. Finally, the corrected-percentage value of HOCl is multiplied by the input FAC data to provide at the output of the computer a value representing the HOCl content.

OUTLINE OF DRAWINGS

For a better understanding of the invention as well as other objects and further features thereof, reference is made to the following detailed description to be read in conjunction with the accompanying drawings, wherein:

FIG. 3 is a block diagram of a digital analyzer in accordance with the invention for measuring the hypochlorous acid content of chlorinated water being tested.

DETAILED DESCRIPTION OF INVENTION

The Factors Involved

Chlorination, as previously explained, gives rise in the water being treated to both free available chlorine (FAC) and combined available chlorine. Free available chlorine has a hypochlorous acid component (HOCl) that is a highly reactive disinfectant and a hypochlorite ion component (OCl$^-$) that is much less reactive. The two components are related to each other by the following chemical reaction which represents a system in dynamic equilibrium:

$$HOCl \rightleftharpoons H^+ + OCl^- \quad (1)$$

The relationships that exist between HOCL, FAC and the pH of chlorinated water is well known. These relationships are expressed by the following equations in which the fraction $\alpha$ represents the HOCl component of FAC:

$$\alpha = \frac{(HOCl)}{FAC} \quad (2)$$

$$\alpha = \frac{(HOCl)}{(HOCl) + OCl} \quad (3)$$

-continued $$\alpha = \frac{(H + D)}{(H^+) + K} \quad (4)$$

In the last equation, the term (H$^+$) represents the concentration of hydronium ions or the acidity of the solution. The term K is the equilibrium constant for the HOCl reaction expressed by the first equation.

Since the term H$^+$ is a function of pH, it is obvious that fraction $\alpha$ is also a function of the pH factor. Thus at low pH levels, free available chlorine residuals consist predominantly of HOCl, whereas above pH 7.5, OCl$^-$ predominates, while above pH 9.5, free available chlorine residuals consist almost entirely of OCl$^-$.

The term K, on the other hand, is a function of temperature, values of which are known from 0° C. to 35° C. The values for K, published by J. C. Morris, *J. Physical Chem* 70: 3798 (1966), are generally accepted as accurate.

Figures 1, 2:
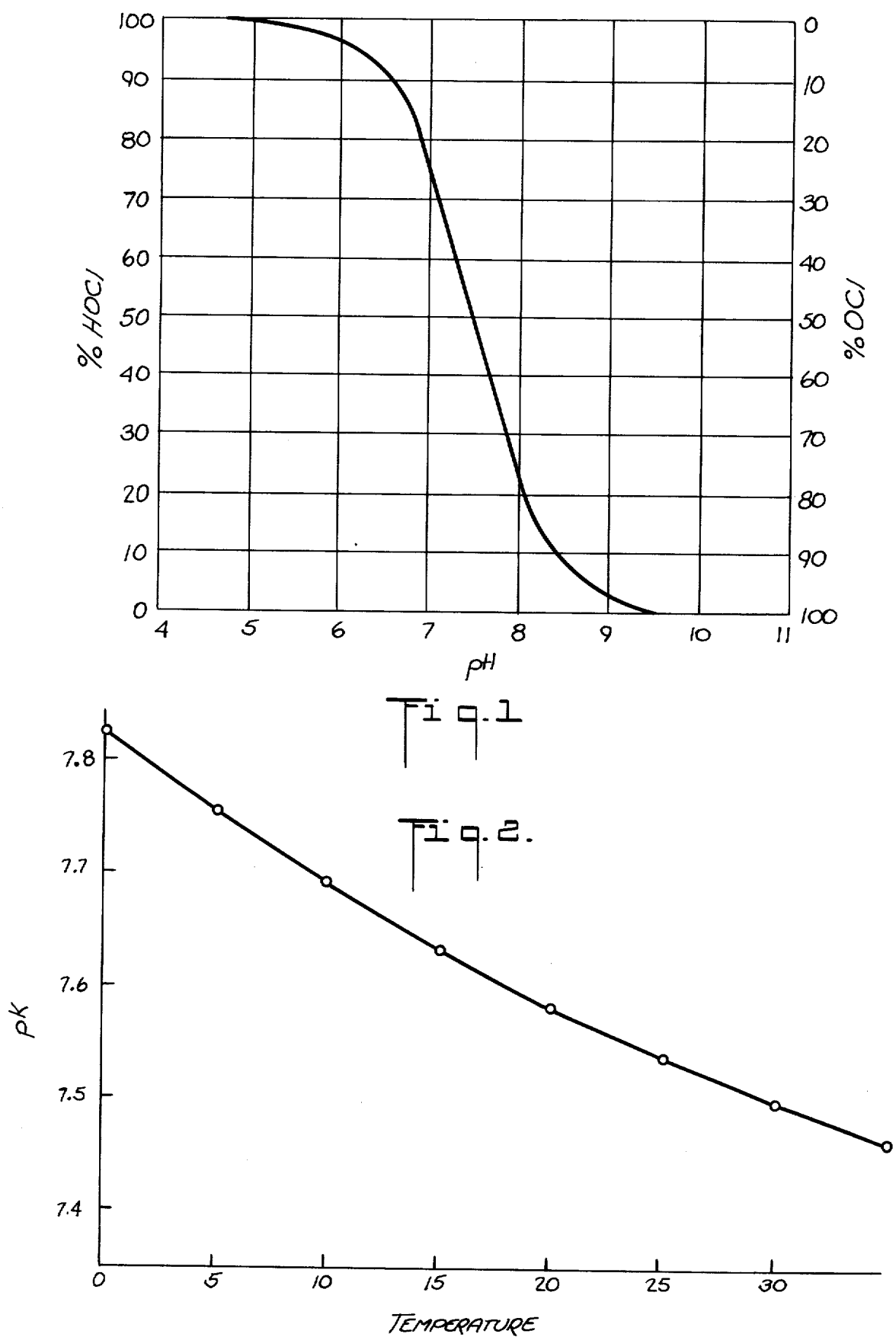
FIG. 1 is a graph illustrating the known relationship existing between the percentage of HOCl and OCl$^-$ at a reference temperature in a range of pH value.
FIG. 2 is a graph illustrating the relationship existing between HOCl and its equilibrium constant K.
Figure 2:
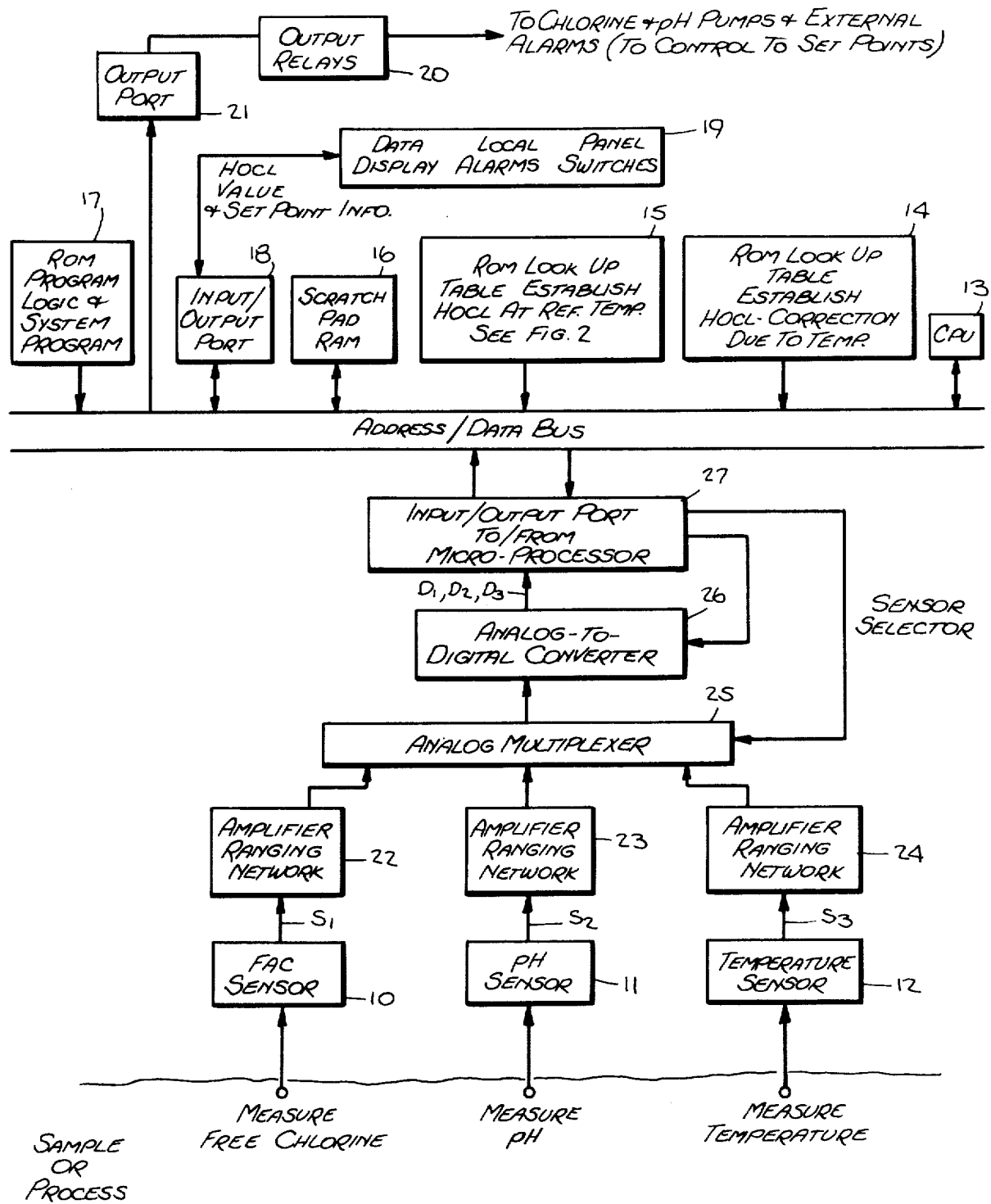

The relationship existing at a reference temperature between the percentage of HOCl and OCl$^-$ in a range of pH values is graphically illustrated in FIG. 1, where it will be seen that as the pH rises from pH 4 to pH 10, the percentage of HOCl drops from 100% to 0%, while the percentage of OCl$^-$ rises from 0% to 100%. Thus there is a well-defined relationship between the ratio of HOCl and OCl$^-$ at various pH levels.

There is also a well-defined relationship between temperature and the equilibrium constant for HOCl. This is shown graphically in FIG. 2 where pK (pK = log K) is plotted against temperature. Thus while at the reference temperature (FIG. 1) there is an established ratio between the HOCl and OCl$^-$ components of free available chlorine, the HOCl content is modified when the temperature departs from the reference level.

In order, therefore, to arrive at the HOCl content of chlorinated water containing free available chlorine, one must take into account three factors; namely, the FAC content, pH factor and water temperature.

The Sensors

In a digital analyzer in accordance with the invention as shown in FIG. 3, a sample of the chlorinated water to be tested is sensed by three probes, 10, 11 and 12. Probe 10 is adapted to sense the free available chlorine residual of the sample and to produce an analog signal $S_1$ representative of the FAC content. For this purpose, use may be made of a standard, commercially-available probe, such as the "Anachlor" transmitter previously identified. This is an amperometric-type analytical instrument that continuously measures the concentration of free available chlorine residual in a process stream or tank and produces a 4 to 20 mAdc output signal that is directly proportional to the free chlorine in terms of parts per million (mg/1) by weight.

Probe 11 is adapted to sense the pH factor of the sample (in a range of 2 to 14) and to produce an analog signal $S_2$ representative thereof. For this purpose, one may use a standard commercially-available instrument such as the pH measurement system manufactured and sold by Fischer & Porter of Warminster, Pa. and described in their Instruction Bulletin 17PH1000 (1976). This instrument consists of a pH sensor having a measuring electrode and a counter electrode and a pH transmitter which acts to produce a current signal compensated for changes in process liquid temperatures. The signal produced by this sensor is converted into a 4 to 20 mAdc signal.

Probe 12 is adapted to sense the temperature (T) of the sample (in a range of 10° to 50° C.) and to produce an analog signal $S_3$ representative thereof. For this purpose, use is preferably made of a standard temperature transducer that exhibits changes in electrical resistance proportional to changes in temperature to produce an analog signal in the 4 to 20 mAdc range representative of the temperature of the sample. Suitable for this purpose is the YSI-Sostman platinum resistance elements manufactured by the Yellow Springs Instrument Co. of Yellow Springs, Ohio, in combination with a suitable current transmitter.

The Computer

The three analog signals $S_1$, $S_2$ and $S_3$ produced by sensors 10, 11 and 12 are fed into a digital computer in accordance with the invention to determine the HOCl content of the sample being tested. But before the structure and operation of this computer is described, a brief review of digital computers generally may be helpful.

A digital computer is a machine capable of carrying out arithmetic or logic operations on digital data entered into its input and of yielding at its output numerical results or decisions. All digital computers, whether in large-scale general-purpose form or in micro-computer form, are essentially composed of a central processing unit, a memory system and input-output devices.

The task assigned to a central processing unit (CPU) is to receive and to store for later processing, data in the form of binary digits or bits (0's or 1's), to perform arithmetic or logic operations on this data in accordance with previously-stored instructions, and to deliver the results to the user of the computer through a read-out device such as an electric typewriter or a cathode ray display tube. Thus a digital computer may be used in conjunction with industrial process control loops to compare the process variable in each loop with a set point and to provide an output signal which depends on the deviation of the variable from the set point. The output signal is used to govern a final control element such as a valve or pump in the process loop to cause the variable to change in a direction and to an extent bringing the variable in line with the set point.

The number of digits or bits needed to represent a computer instruction or the number of bits needed to represent the largest data element normally processed by the computer is referred to as a "word." The number of bits that a computer is capable of processing as a unit is known as a "byte." A byte may be equal to or less than the number of bits in a word; hence both an 8-bit or a 16-bit word-length computer is capable of processing data in 8-bit bytes.

The central processing unit is that component of the computer which controls the interpretation and execution of instructions. In general, a CPU contains the following elements: "Control" which includes logic and instructions for decoding and executing the program stored in "memory"; "Registers" which provide control with temporary storage in the form of random-access memories (RAM's) and their associated functions; an Arithmetic and Logic Unit (ALU) that performs arithmetic and logic operations under supervision of control.

A microprocessor is the central processing unit of a computer with its associated circuitry that is scaled down by integrated-circuit techniques to fit on one or more silicon chips containing thousands of transistors, resistors or other electronic circuit elements. By combining a microprocessor with other integrated circuit chips that provide timing, random access memory, interfaces for input and output signals and other ancillary functions, one can thereby assemble all of the necessary components of a mini-computer whose master component is the microprocessor.

The memory system is that component of a computer which holds data and instructions, each instruction or datum being assigned a unique address that is used by the CPU when fetching or storing the information. There are three distinct types of memories, each of which in a mini-computer can be reduced to a single silicon chip. The read-only memory or ROM is a memory adapted to store information permanently, such as a math function or a micro-program (a special purpose program initiated by a single instruction in the system's main program). A memory that can be programmed by the user, but only once, is known as a programmable ROM or PROM; hence when a PROM is programmed, it then functions as a ROM.

The term read/write memory signifies that the memory is capable of storing information (write) and of retrieving the stored information (read) at an identical or similar rate. In a computer, a random-access memory (RAM) is a read-write memory adapted to store information in such a way that each bit of information can be retrieved within the same amount of time as any other bit.

The capability of a computer depends in good part on storage capacity of its memory system. The amount of information stored ranges from fewer than 100 bits to more than a billion bits for a large scale computer. Integrated-circuit memories based on transistors are designed to store bits or binary digits on a chip. Currently, the most advanced RAM chip that is available commercially has a maximum storage capacity of 16,384 bits.

The basic "hardware" components of a digital computer are the central processing unit (CPU), the memory system and the input-output (I/O) device. The registers, the control and the arithmetic logic unit of the CPU is linked with the memory system and the I/O device by a data bus; that is, a group of wire that allows the memory, the CPU and the I/O to exchange "words."

The "software" associated with a computer are those expedients by which the computer is explicitly told what to do through a step-by-step sequence of individual instructions which together constitute a program to perform some specific function to yield a solution to a specific problem. An "instruction" is a group of bits that define a particular computer operation. Thus an arrangement may direct a computer to move data, to carry out arithmetic and logic operations, to control I/O devices, or to make a decision as to which instruction is to be executed next.

In FIG. 3, the computer includes a microprocessor or CPU 13, which is the heart of the instrument, for it decodes instructions and performs the necessary computations. There are many microprocessors presently on the market capable of performing the function of CPU 13 to compute the HOCl content, these ranging from small 4-bit devices to 16-bit super-fast microprocessors.

The present trend is toward 8-bit systems. Suitable for CPU 13 is an INTEL 8080A or an INTEL 8085, these being 8-bit machines. Also acceptable are a Motorola 6800, an 8-bit machine similar to INTEL's 8080A and a Fairchild F8, an 8-bit machine in which a complete processor is provided on two chips.

Associated with CPU 13 is a ROM 14 having a look-up table which stores the relationship known to exist at a reference temperature between the percentage of HOCl and the percentage of OCl⁻ in a range of pH values (the relationship illustrated in FIG. 1).

Also associated with CPU 13 is a ROM 15 having a look-up table which stores the relationship known to exist between temperature variations and the equilibrium constant K for HOCl, this relationship being illustrated in FIG. 2. This table may be used on the known relationship between temperature variations (5° to 30° C.) and the Acid Ionization Constant of HOCl, as disclosed in the article of J. C. Morris in the Journal of Physical Chemistry of December 1966.

Scratch pad RAM 16 is a memory that is used to temporarily store intermediate results so that this data can be retrieved quickly when needed. The ROM 17 (Program Logic and System Programming) is used to store the instructions in order to operate the instrument and control the external pumps and feeders. ROM 17 contains the basic software instructions in order to input data from sensors 10, 11 and 12, perform the necessary data manipulations, output the HOCl content value and perform the control functions in a manner later explained in connection with the software in FIG. 4.

The computer is linked by input/output ports 18 to an assembly 19 providing data display, local alarms and panel switches which together constitute the operator's access to the instrument, making it possible for the operator to read the HOCl value, to determine which pumps are on, to respond to alarms and to change set point values in an automatic process control system associated with the computer.

Output relays 20 are coupled to the computer through output port 21, these relays serving to control the chlorine and pH pumps, so that the instrument can regulate the HOCl value. One can also wire external alarms to the contacts of these relays.

The above-identified components are coupled to each other and to the input data sensors by an address/data bus serving as a communication link between the components of the system to facilitate the exchange of "words" therebetween. The analog signals $S_1$, $S_2$ and $S_3$ from sensors 10, 11 and 12 are fed through respective amplifiers 22, 23, and 24 to the input of an analog multiplexer 25. The function of these amplifiers is to provide amplification of the respective sensor outputs, to afford normalized signal levels to multiplexer 25, and to provide local temperature compensation for the FAC sensor 10 and pH sensor 11. Alternatively, temperature compensation may be effected using a system temperature sensor and appropriate software.

Multiplexer 25 serves to select either the FAC analog signal $S_1$ from sensor 10, the pH value analog signal $S_2$ from sensor 11, or the T value analog signal $S_3$ from sensor 12 as an input to the microprocessor. The selected analog signal, after first being converted by an analog-to-digital converter 26 into digital data ($D_1$, $D_2$ or $D_3$) is then fed through the input/output port 27 to and from the microprocessor. To reduce cost, the analog signals are time-multiplexed and sampled at regular time intervals.

When a particular analog value ($S_1$, $S_2$ or $S_3$) derived from sensors 10, 11 and 12 is presented to analog-to-digital converter 26, this analog value is changed to a corresponding digital value ($D_1$, $D_2$, or $D_3$) so that it can be processed by the digital computer. The resolution of the converter and its conversion speed is such as to provide the necessary accuracy and sample updates.

Operation of Computer

Figure 4:
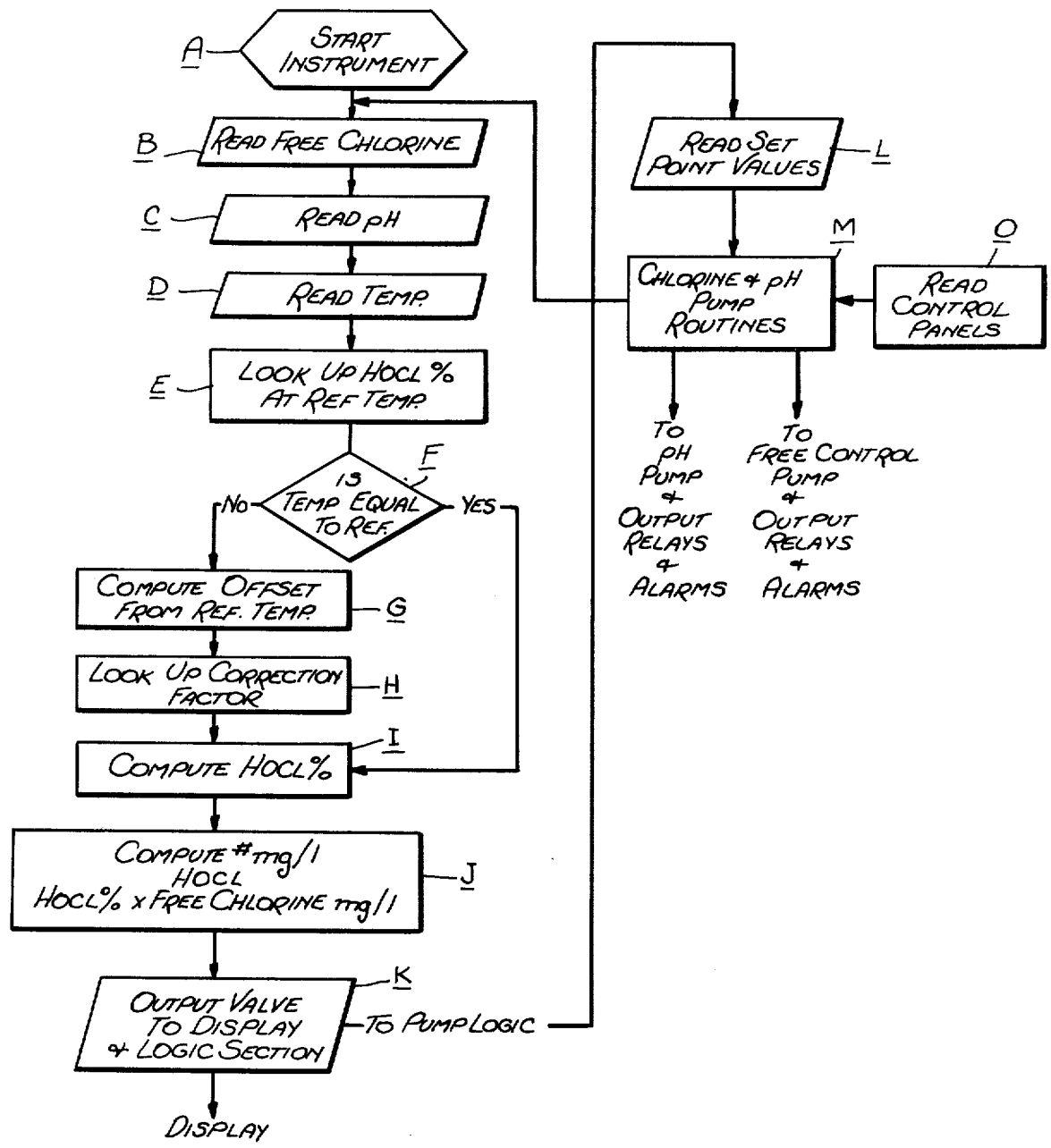
FIG. 4 is a diagram of the software of the digital analyzer.

Referring now to FIG. 4, which is a diagram of the basic software of the digital HOCl analyzer, we shall now trace the step-by-step program provided by the set of instructions to show how the sensed values of free available chlorine content, pH factor and temperature provide input data which is operated upon or manipulated in the computer to determine the HOCl content.

Step A initiates operation of the instrument, this being followed in sequence by step B which is to read the free available chlorine content to produce input FAC data $D_1$, step (C) which is to read the pH value to produce input pH data $D_2$, and step D which is to read the temperature value to produce input T data $D_3$, the data derived from these readings being stored preparatory to their manipulation.

The next step E is to look up in ROM 14 the table which establishes the percentage of HOCl at a reference temperature for the pH value of data $D_2$. In step F, the value of T in data $D_3$ is compared with the reference temperature, and if these temperatures differ, an instruction is given in step G to compute the necessary offset from the established percentage of HOCl. This is carried out in step H by looking up the correction factor for the sensed temperature value in ROM 15, this being followed in step I by a computation of the temperature-corrected percentage of HOCl. If, however, in step F, it is found that the sensed temperature matches the reference temperature, then steps G, H and I are bypassed, for the computation of the HOCl percentage required no correction.

In step J, the HOCl content (# mg/1) is determined by multiplying the HOCl percentage value yielded by step I with the FAC input data $D_1$. Step K supplies the resultant of step J to a suitable display. The HOCl content reading is also supplied to the pump logic, where in step L it is compared with set point values in order to regulate in step M the pumps controlling the chlorine feed in the chlorinator treating the process water as well as the pumps controlling pH, thereby to automatically maintain a desired level of HOCl content. Step O activates the read control panel.

While there has been shown and described a preferred embodiment of a digital hypochlorous acid analyzer in accordance with the invention, it will be appreciated that many changes and modifications may be made therein without, however, departing from the essential spirit thereof. Thus the instrument can be used not only for measuring but for controlling the HOCl content of a given process as well. The control section of the instrument operates the three chlorine pumps, pH pumps, output relays and alarms. Using flexible softwave, this instrument can function in almost any control scheme and adhere to locate, state and Federal requirements.

I claim:

1. An analyzer for continuously and accurately determining the hypochlorous acid content of chlorinated water containing free available chlorine having a hypochlorous acid component (HOCl) which is highly reactive, and a hypochlorite ion component (OCl⁻) which is a less reactive disinfectant, said analyzer comprising:

first second and third probes to sense respectively the free available chlorine content (FAC), the pH factor and temperature in a sample of the chlorinated water to produce respective analog signals representative of these variables;

means to convert said analog signals into corresponding digital input data; and a digital computer responsive to said input data to produce output data indicative of the HOCl content of the sample, said computer including a first memory storing the relationship existing at a reference temperature between the percentage of HOCl and OCl$^-$ in a predetermined range of pH values, and a second memory storing the relationship existing between temperature and the equilibrium constant of HOCl, means consulting the first memory and responsive to the input pH data to establish the percentage of HOCl in the sample, means consulting the second memory and responsive to the input T data to correct the established percentage of HOCl to produce a temperature-corrected HOCl percentage value, and means to multiply the temperature-corrected percentage value with the input FAC data to produce an output representing the HOCl content.

2. An analyzer as set forth in claim 1, wherein said first probe includes an amperometric cell through which said sample flows to produce a signal representing the FAC content of the sample.

3. An analyzer as set forth in claim 1, wherein said second probe includes a pH measuring electrode and a counter electrode, said probe being compensated for temperature.

4. An analyzer as set forth in claim 1, wherein said third probe includes a resistance element whose resistance varies as a function of temperature.

5. An analyzer as set forth in claim 1, wherein said first memory is a read-only-memory.

6. An analyzer as set forth in claim 1, wherein said second memory is a read-only-memory.

7. An analyzer as set forth in claim 1, wherein said analog signals are sequentially applied to an analog-to-digital converter to produce said corresponding digital input data.

8. An analyzer as set forth in claim 7, wherein said analog signals are applied to said converter sequentially by a multiplexer.

9. An analyzer as set forth in claim 1, wherein said multiplication is carried out in said computer by a microprocessor.

* * * * *